United States Patent
Kirchner

(10) Patent No.: US 9,585,571 B2
(45) Date of Patent: Mar. 7, 2017

(54) METHOD AND IMPLANTABLE MEDICAL SYSTEM FOR MONITORING RESPIRATORY PARAMETERS AND A CORRESPONDING COMPUTER PROGRAM AND A CORRESPONDING COMPUTER-READABLE STORAGE MEDIUM

(75) Inventor: Jens Kirchner, Erlangen (DE)

(73) Assignee: BIOTRONIK SE & CO. KG, Berlin (DE)

( * ) Notice: Subject to any disclaimer, the term of this patent is extended or adjusted under 35 U.S.C. 154(b) by 861 days.

(21) Appl. No.: 13/565,792

(22) Filed: Aug. 2, 2012

(65) Prior Publication Data
US 2013/0046189 A1 Feb. 21, 2013

Related U.S. Application Data

(60) Provisional application No. 61/524,351, filed on Aug. 17, 2011.

(51) Int. Cl.
*A61B 5/0215* (2006.01)
*A61B 5/08* (2006.01)

(52) U.S. Cl.
CPC .......... *A61B 5/0215* (2013.01); *A61B 5/0816* (2013.01); *A61B 2562/0219* (2013.01)

(58) Field of Classification Search
CPC ... A61B 5/0205; A61B 5/0215; A61B 5/0816; A61B 2562/0219
See application file for complete search history.

(56) References Cited

U.S. PATENT DOCUMENTS

| | | | |
|---|---|---|---|
| 6,350,242 B1 | 2/2002 | Doten et al. | |
| 2003/0093125 A1* | 5/2003 | Zhu et al. | 607/25 |
| 2010/0100000 A1* | 4/2010 | Lee et al. | 600/538 |

FOREIGN PATENT DOCUMENTS

| | | |
|---|---|---|
| EP | 2008581 A2 | 12/2008 |
| EP | 2030564 A2 | 3/2009 |

OTHER PUBLICATIONS

European Search Report dated Jan. 7, 2013, 6 pages.

* cited by examiner

*Primary Examiner* — Michael Kahelin
*Assistant Examiner* — Tho Tran
(74) *Attorney, Agent, or Firm* — ARC IP Law, PC; Joseph J. Mayo

(57) ABSTRACT

A method and an implantable medical system for monitoring respiratory parameters, and a corresponding computer program and a corresponding computer-readable storage medium which can be used in particular for monitoring, especially for remote monitoring of the health condition of a patient with cardiac insufficiency that provides an improved method for determining the functional capacity of the cardiovascular system with consideration for stress.

19 Claims, 3 Drawing Sheets

METHOD AND IMPLANTABLE MEDICAL SYSTEM FOR MONITORING RESPIRATORY PARAMETERS AND A CORRESPONDING COMPUTER PROGRAM AND A CORRESPONDING COMPUTER-READABLE STORAGE MEDIUM

This application claims the benefit of U.S. Provisional Patent Application 61/524,351 filed on 17 Aug. 2011, the specification of which is hereby incorporated herein by reference.

BACKGROUND OF THE INVENTION

Field of the Invention

At least one embodiment of the invention relates to a method and an implantable medical system for monitoring respiratory parameters, and a corresponding computer program and a corresponding computer-readable storage medium, which can be used in particular for monitoring, especially for the remote monitoring of the health condition of a patient with cardiac insufficiency.

Description of the Related Art

Solutions are already known in the field of the invention, in the case of which impedance and blood pressure signals are evaluated for monitoring the health condition. The disadvantage of the previous solutions in particular is that the patient's stress state is not taken into account in the known methods.

BRIEF SUMMARY OF THE INVENTION

It is therefore a feature of at least one embodiment of the invention to provide a method and an implantable medical system for monitoring respiratory parameters, and a corresponding computer program and a corresponding computer-readable storage medium which avoid the disadvantages of the conventional solutions and, in particular, provide an improved method for determining the functional capacity of the cardiovascular system with consideration for stress.

The problem is solved by a medical system, by a method, by a computer program, and a computer-readable storage medium as claimed herein.

The implantable medical system comprises at least one pressure sensor, a time-registration unit, and a data processing unit, wherein the system is designed such that the following steps can be carried out:
  register blood pressure values, at least temporarily,
  evaluate the registered blood pressure values to determine data that describe a load,
  evaluate the registered blood pressure values to determine data that describe respiration,
  evaluate respiration to determine a diagnostic quantity depending on the data that describe the load.

The step to "evaluate respiration to determine a diagnostic quantity depending on the data that describe the load" relates both to the dependence of respiration on the data that describe the load, and the dependence on the data from respiration that describe the load.

A particular characteristic of the method according to the invention, inter alia, is that the load on the patient is detected and evaluated in addition to parameters that are usually evaluated when monitoring cardiac insufficiency. The method according to the invention therefore offers the particular advantage that this is achieved without the use of additional devices such as reference sensors. Thus, in the method according to the invention, only a blood pressure measurement is carried out to monitor the respiratory parameters. At least one pressure sensor is used for this purpose, wherein the at least one pressure sensor is preferably disposed in the pulmonary artery and/or the aorta and/or the peripheral arteries and/or the peripheral veins and/or the veins close to the heart and/or the ventricles. The at least one pressure sensor detects signals at least temporarily, and preferably continuously, and the signals that are detected are evaluated to determine blood pressure values or values associated with blood pressure. Furthermore, at least one data processing unit is used at the least to determine the blood pressure values. Preferably, the at least one data processing unit is also used to determine—from the signals that were detected or the blood pressure values that were determined—data (stress values) that describe a load, in particular a physical load on the patient, or that are associated with the load. For example, heart rate can be extracted from the signals detected by the at least one pressure sensor, which is used to describe the patient's load or activity. Furthermore, according to at least one embodiment the invention, data are determined—on the basis of the detected signals or blood pressure values that were determined—which describe respiration or are connected to respiration. In a preferred embodiment, this takes place by evaluating characteristic points of the blood pressure signal. These characteristic points can be at least one of the following features, for example:
  beginning of a systole,
  end of a systole,
  maximum pressure within one cardiac cycle,
  minimum pressure within one cardiac cycle,
  extreme values of the first derivative of the blood pressure.

The respiratory signal is determined on the basis of the characteristic points, e.g. the points in time when the systoles start, or the maximum pressures of the cycles. This is possible, in particular, because the values of blood pressure represent a superposition of blood pressure variations of the respiratory cycle and those of heart contraction. The characteristic points can therefore be considered a good approximation of respiration. In a preferred embodiment, threshold values are used to determine the data that describe respiration.

According to at least one embodiment of the invention, at least one characteristic value is determined from the data that are associated with respiration. This at least one characteristic value can be one of the following features of the respiratory signal, for example:
  frequency,
  frequency variability,
  amplitude,
  maximum slope,
  minimum slope,
  number of peaks per respiratory cycle,
  number of plateaus per respiratory cycle,
  duration of the increase,
  duration of the decrease,
  duration of the pause between two cycles, i.e. the time in which no change in thoracic pressure is determined,
  integral of one respiratory cycle.

According to at least one embodiment of the invention, at least one diagnostic quantity is derived from the at least one characteristic value, which describes the dependence of respiration on the load value. The at least one diagnostic quantity preferably comprises parameters of a curve of the at least one characteristic quantity as a function of the load.

The at least one diagnostic quantity can be at least one of the following parameters, for example:
- mean, minimum, and/or maximum slope of the curve;
- mean, minimum, and/or maximum slope of the curve in a defined load range;
- value of the load at an inflection point, from which point forward the curve has a constant value;
- fit parameters of a defined fit function;
- location and width of a load range in which the curve exhibits a defined functional dependence.

In a preferred embodiment of the invention, the data that are associated with respiration, in particular the at least one characteristic quantity, which were determined for various loads are compared with each other.

In a further preferred embodiment, the value range of the data that describe the load is subdivided into intervals (load intervals) having a specifiable length. In a preferred embodiment, a variable length is assigned to these intervals. Alternatively, the same length can always be specified. Preferably, a load stage is ascribed to at least one part of the intervals. The ascribed load stage can be taken from a defined value range, for example, such as the mean load of a load interval, or, if discrete load values are involved, the ascribed load stage can be taken from a defined quantity of values.

In another preferred embodiment, time intervals are determined as a function of the load. In a preferred embodiment, the length of the time interval is determined such that the patient is located exclusively at one load stage within a time interval, i.e. within a time interval, only that type of data (load data) were registered that lie in the same load interval. On the basis of the load stages ascribed to the load intervals, it is now possible to evaluate time intervals that include predefined load values. In particular, data that are associated with respiration can be evaluated. According to an evaluation used as an example, for a quantity of time intervals, the mean of at least one part of these data associated with respiration is calculated. In an embodiment used as an example, the evaluation includes all time intervals of a day that comprise load values of a predefinable load stage. For example, a daily mean value for respiratory frequency can be calculated for each load stage.

The time intervals can be determined using the time-registration unit.

In order to determine the time intervals, the change in load is preferably monitored. By evaluating the change in the load, points in time are detected at which the load transitions from one load interval to another. The points in time that are detected define the time intervals. It is thus possible to consider only those intervals in an evaluation of respiratory parameters in which the load does not leave a value range for a defined period of time. Respiratory parameters can therefore be evaluated as a function of a load stage.

In a further preferred embodiment, the at least one diagnostic quantity is derived from the curve by fitting. In particular, fit parameters such as slope and/or offset, time constants, or the like can be evaluated. Alternatively, at least one diagnostic quantity is obtained from the curve by fitting at least two fit functions at a specifiable region of the curve which describes the behavior of the characteristic value of respiration as a function of the load, and determining and evaluating the quality of the fit and/or fit parameters. In particular, for example, the type of the optimal fit function and/or a quantity derived from a vector of the fit quality can be evaluated.

The fitting of a fit function for determining an optimal fit parameter, and the test to determine which fit function from a quantity of templates is optimal are two different approaches. When a single function is fitted, a certain shape (fit function) is presupposed, and the special property, i.e. the fit parameter, is of interest. When testing various functions, the shapes to be expected are unknown, and various possibilities are tested. The result is a decision as to which shape fits the best. The associated fit parameters are usually less interesting. Above all, a free parameter of a certain fit function can be located in a completely different value range in another fit function, or can even be undefined or unmeaningful.

In another preferred embodiment, the load data are registered by an activity sensor.

A further aspect of the invention relates to an implantable system comprising at least one pressure sensor, a time-registration unit, and at least one data processing unit, and is designed such that a method for monitoring respiratory parameters can be carried out, wherein blood pressure values are detected at least temporarily, data that describe the load and data that describe the respiration are determined on the basis of the blood pressure values that were registered, and at least one diagnostic quantity is determined from the evaluation of the data describing the respiration as a function of the data that describe the load.

Another preferred embodiment of the implantable system also comprises at least one activity sensor and is designed such that a method for monitoring respiratory parameters can be carried out, wherein signals of the at least one activity sensor are registered and at least one load value is determined by evaluating the signals of the activity sensor, and wherein, furthermore, blood pressure values are registered at least temporarily, data that describe respiration are determined on the basis of the blood pressure values that were registered, and at least one quantity is determined from the evaluation of the data describing respiration as a function of the data describing the load.

In a preferred embodiment of the implantable system, the at least one pressure sensor is preferably disposed in the pulmonary artery and/or the aorta and/or the peripheral arteries and/or the peripheral veins and/or the veins close to the heart and/or the ventricles.

For the rest, the corresponding implantable systems are provided for each of the particular embodiments of the method according to the invention that were described.

To evaluate the blood pressure signal at times of a defined load, an implantable system is provided in a preferred embodiment, which comprises at least
- one activity sensor,
- one blood pressure sensor, and
- one data processing unit as evaluation unit, and is designed to perform the following tasks:
a) measure a signal that is associated with the physical load,
b) measure a signal that is associated with a blood pressure,
c) determine at least one time interval for signal evaluation using the load signal,
d) perform the following steps for each of the time intervals determined in c):
   (i) determine characteristic points in the blood pressure signal,
   (ii) determine a signal associated with respiration from the points determined in step (i),
   (iii) determine a characteristic value from the signal determined in step (ii), e) determine a diagnostic quantity from the quantity of values determined in step d), by averaging, for example.

To compare the characteristic values at different loads, an implantable system is provided in a preferred embodiment that comprises at least
one activity sensor,
one blood pressure sensor, and
one data processing unit as evaluation unit,
and is designed to perform the following tasks:
a) measure a signal that is associated with the physical load,
b) measure a signal that is associated with a blood pressure,
c) determine a plurality of time intervals for signal evaluation, possibly using the load signal,
d) perform the following steps for each of the time intervals determined in c):
(i) ascribe a load value to the time interval,
(ii) determine characteristic points in the blood pressure signal,
(iii) determine a signal associated with respiration from the points determined in step (ii),
(iv) determine a characteristic value from the signal determined in step (iii),
e) determine a diagnostic quantity from the data pairs of load (step (i)) and characteristic value of respiration (step (iv)) generated in step d).

After having been loaded into memory means of a data processing device, a computer program according to at least one embodiment of the invention makes it possible for the data processing device to implement a method for monitoring respiratory parameters, wherein
blood pressure values are registered, at least temporarily,
data that describe a load are determined by evaluating the blood pressure values that were registered,
data that describe respiration are determined by evaluating the blood pressure values that were registered,
a dependence of respiration on the data describing the load, or a dependence of the data describing the load on respiration is evaluated to determine a diagnostic quantity.

After having been loaded into memory means of a data processing device, another computer program according to at least one embodiment of the invention makes it possible for the data processing device to implement an alternative method for monitoring respiratory parameters, wherein
signals from at least one activity sensor are registered, at least temporarily, and data that describe a load are determined by evaluating the signals of the at least one activity sensor,
blood pressure values are registered, at least temporarily,
data that describe respiration are determined by evaluating the blood pressure values that were registered,
a dependence of respiration on the data describing the load, or a dependence of the data describing the load on respiration is evaluated to determine a diagnostic quantity.

According to a further preferred embodiment of the invention, the computer program is modular, wherein individual modules are installed on various parts of the data processing device.

According to advantageous embodiments, additional computer programs are provided that can implement further method steps or method sequences that are mentioned in the description.

Computer programs of this type can be provided for downloading (for a fee or free of charge, or in a freely accessible or password-protected manner) in a data network or communication network. The computer programs provided in this manner can then be utilized by a method by downloading a computer program from an electronic data network such as the Internet onto a data processing device that is connected to the data network.

To implement the method for monitoring respiratory parameters according to at least one embodiment of the invention, a computer-readable memory medium is used, on which a program is stored that enables a data processing device—once said program has been loaded into memory means of the data processing device—to implement a method for monitoring respiratory parameters, wherein
blood pressure values are registered, at least temporarily,
data that describe a load are determined by evaluating the blood pressure values that were registered,
data that describe respiration are determined by evaluating the blood pressure values that were registered,
a dependence of respiration on the data describing the load, or a dependence of the data describing the load on respiration is evaluated to determine a diagnostic quantity.

According to at least one embodiment of the invention, a computer-readable memory medium is also provided, on which a program is stored that enables a data processing device—once said program has been loaded into memory means of the data processing device—to implement a method for monitoring respiratory parameters, wherein
signals from at least one activity sensor are registered, at least temporarily, and data that describe a load are determined by evaluating the signals of the at least one activity sensor,
blood pressure values are registered, at least temporarily,
data that describe respiration are determined by evaluating the blood pressure values that were registered,
a dependence of respiration on the data describing the load, or a dependence of the data describing the load on respiration is evaluated to determine a diagnostic quantity.

At least one embodiment of the invention can be used to particular advantage for monitoring cardiac insufficiency via shortness of breath.

As the state of health worsens in a patient with cardiac insufficiency, the capacity of the cardiovascular system decreases under stress. At a given load, the capacity can be determined on the basis of respiration (in particular frequency and amplitude, and the shape of the respiratory cycle). The system presented here is composed of an activity sensor which quantifies the load on the patient, and a blood pressure sensor, preferably in the pulmonary artery and/or the aorta and/or the peripheral arteries and/or the peripheral veins and/or the veins close to the heart and/or the ventricles, from the signals of which a respiratory signal is extracted. The evaluation of characteristic values of this respiratory signal as a function of load is used to determine the patient's capacity and, therefore, to monitor the severity of his cardiac insufficiency.

BRIEF DESCRIPTION OF THE DRAWINGS

Advantages and functional characteristics of at least one embodiment of the invention will additionally become apparent hereinafter from the description of exemplary embodiments based on the figures. Shown are.

DETAILED DESCRIPTION OF THE INVENTION

The invention will be described below in greater detail by reference to an embodiment as an example, wherein the invention is not limited to this embodiment, but also comprises solutions, provided these solutions only embody the features of the independent claims.

The embodiment presented as an example is embodied as an implantable system that comprises a blood pressure sensor and an activity sensor. The blood pressure sensor is disposed in the pulmonary artery, and the activity sensor is in the form of an accelerometer.

In the embodiment presented as an example, the invention is integrated in an implantable system for monitoring cardiac output. In addition to the blood pressure sensor and the activity sensor, the system comprises a transmitter and an antenna for transmitting data to external devices.

To implement the method according to the invention, in the embodiment presented as an example, the value range of the activity sensor is subdivided into a plurality of activity levels and stages. Seven stages are provided, for example, specifically "rest", "low", "moderate", "high", and three intermediate stages. The value range can also be subdivided into a greater or lesser number of stages.

It is furthermore provided that disjoint time intervals are determined, in which the patient is situated exclusively in one load stage. In a preferred embodiment, the time intervals have a defined, specified length, such as 2 minutes. Signal 100 of the pulmonary artery pressure (PAP) is now evaluated for each of these 2-minute intervals.

Figure 1:
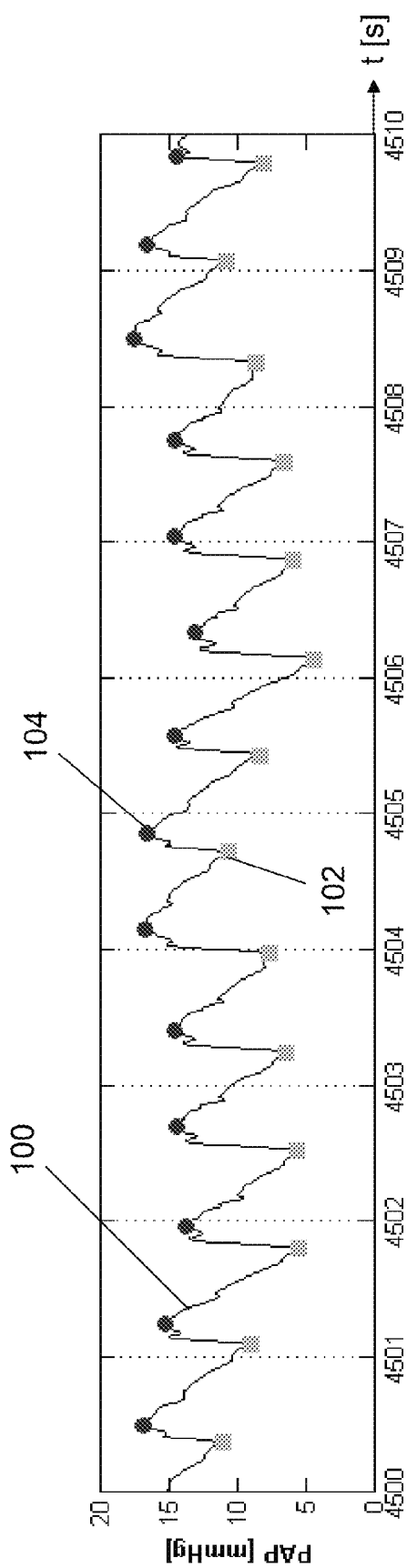
FIG. 1 shows a section, as an example, of a recording of pulmonary artery pressure over time.

FIG. 1 shows a section, as an example, of a recording of PAP signal 100 over time. The respiratory signal is reconstructed by evaluating PAP signal 100. For this purpose, in this embodiment presented as an example, the systole of each cycle is evaluated as a characteristic point of start instant 102. Alternatively, pressure maximum 104 of each cycle can also be evaluated. The pressure values of start instants 102 over time are the reconstructed respiratory signal. A baseline shift may be required.

Figure 2:
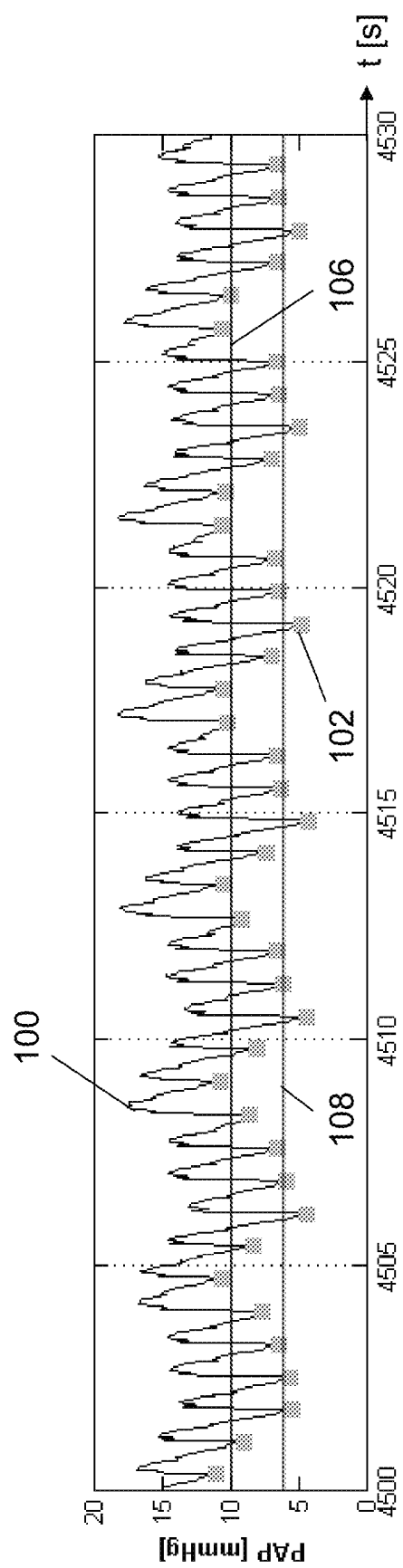
FIG. 2 shows a section, as an example, of a recording or the pulmonary artery pressure over time, with threshold values indicated.

In the reconstructed respiratory signal, cycle detection is carried out, wherein a threshold criterion is preferably used, as illustrated in FIG. 2 using the two horizontal lines 106, 108 which represent the two threshold values. FIG. 2 illustrates that the respiratory signal is determined from start instant 102 of the systole of each cycle.

Characteristic values of respiration, such as respiratory frequency, are determined on the basis of knowledge of the respiratory cycle. To obtain the at least one diagnostic quantity, in the embodiment presented as an example, the respiratory frequency is averaged over all intervals of the same load stage. This averaging is preferably carried out for all load stages.

Figure 3:
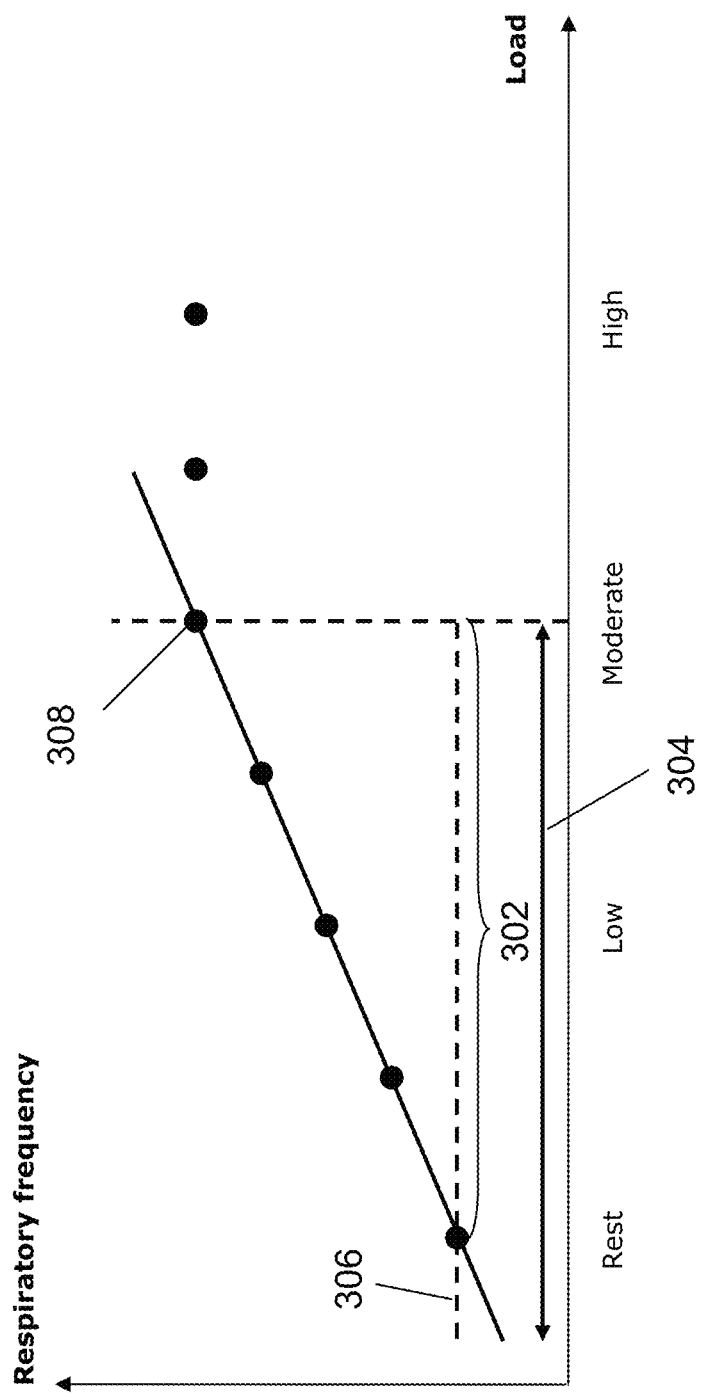
FIG. 3 shows a schematic plot of the value pairs of mean respiratory frequency-physical load.

Value pairs result from this averaging (mean respiratory frequency—load stage) and are plotted as a function of load, as illustrated in FIG. 3. FIG. 3 shows a schematic plot 300 of the value pairs (mean respiratory frequency—load stage), wherein the load is subdivided into seven stages ("rest", "low", "moderate", "high", and three intermediate stages).

Characteristic values that can be derived from this plot 300 are, for example, the slope of plot 300 in linearly increasing range 302, width 304 of linearly increasing range 302, resting respiratory frequency 306, inflection point 308.

As mentioned, in another embodiment presented as an example, the load signal is extracted from the PAP signal. The use of an activity sensor is not necessary in this embodiment presented as an example. Instead, heart rate is extracted as a measure of activity and respiratory frequency or amplitude as a characteristic value of respiration.

In another alternative embodiment, other characteristic values are used to describe respiration instead of or in addition to respiratory frequency. Such alternative characteristic values can be, for example, the slope of the curve, the number of peaks and/or plateaus within one respiratory cycle, the amount of time spent in one certain (relative) value range (e.g. duration of the decrease from 80 to 20% of the maximum pressure difference).

In a further alternative embodiment, the function of the activity sensor is performed by a position sensor, thereby making it possible to differentiate various bodily positions of the patient as "different loads". It is thereby possible in particular to detect orthopnea, i.e. shortness of breath while lying down.

The invention, in its embodiment, is not limited to the preferred embodiments described above. Instead, a number of variants is feasible, which utilize the method according to the invention, the implantable system according to the invention, the computer program according to the invention, or the computer-readable memory medium according to the invention, even in embodiments of fundamentally different types.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable medical system comprising at least
a pressure sensor configured to be disposed in a patient, wherein said pressure sensor at least temporarily and continuously detects blood pressure signals;
a time-registration unit;
a data processing system coupled with said pressure sensor and said time-registration unit;
wherein the data processing system is configured to
register blood pressure values, at least temporarily;
evaluate the registered blood pressure values from said blood pressure signals to determine data that describes a load;
evaluate the registered blood pressure values to determine data that describe respiration;
evaluate said respiration from said data that describes respiration to determine a diagnostic quantity that depends on the data that describes the load;
determine the diagnostic quantity through
a fit of at least two different fit functions to a curve, wherein the curve describes a dependence of the respiration on the data that describes the load, or
a fit function is fit to the curve, wherein the curve describes the dependence of the respiration on the data that describes the load;

determine and evaluate a quality of the fit, wherein a type of shape of the fit, or a quantity derived from a vector of the quality of the fit, or both, is evaluated; and, determine a functional capacity of a cardiovascular system of the patient based on said diagnostic quantity and one or more of said quality of the fit and said quantity derived, to monitor severity of cardiac insufficiency of the patient.

2. The implantable medical system according to claim 1, wherein a heart rate is determined based on the registered blood pressure values and, based on the heart rate, the data that describes the load are determined.

3. The implantable medical system according to claim 1, wherein a value range of the data that describes the load is subdivided into intervals having a specifiable length.

4. The implantable medical system according to claim 3, wherein a load stage is ascribed to at least one part of the intervals wherein the data processing system is further configured to evaluate said respiration to determine a diagnostic quantity that depends on said load stage.

5. The implantable medical system according to claim 1, wherein the time-registration unit is configured to determine at least one time interval as a function of the load.

6. The implantable medical system according to claim 5, wherein the data that describes the respiration are evaluated for at least one part of the at least one time interval.

7. The implantable medical system according to claim 1, wherein said pressure sensor is capable of being disposed in a pulmonary artery or an aorta or peripheral arteries or peripheral veins or veins close to a heart or ventricles.

8. The implantable medical system according to claim 1, wherein the data processing system is further configured to determine fit parameters and start at least one action that depends on the fit parameters.

9. An implantable medical system, comprising:
an activity sensor;
a pressure sensor configured to be disposed in a patient, wherein said pressure sensor at least temporarily and continuously detects blood pressure signals;
a time-registration unit;
a data processing system coupled with said activity sensor, said pressure sensor and said time-registration unit;
wherein the data processing system is configured to
register signals, at least temporarily, of the activity sensor, and determine data that describes a load through evaluation of the signals of the activity sensor,
wherein said data comprises stress values and wherein said load comprises a physical load on said patient;
register blood pressure values from said blood pressure signals, at least temporarily;
evaluate the registered blood pressure values to determine data that describes respiration; and
evaluate said respiration from said data that describes respiration to determine a diagnostic quantity that depends on the data that describes the load;
wherein the data processing system is further configured to
determine the diagnostic quantity through
a fit of at least two different fit functions to a curve, wherein the curve describes a dependence of the respiration on the data that describes the load, or
a fit function is fit to the curve, wherein the curve describes the dependence of the respiration on the data that describes the load;

determine and evaluate a quality of the fit, wherein a type of shape of the fit, or a quantity derived from a vector of the quality of the fit, or both, is evaluated; and, determine a functional capacity of a cardiovascular system of the patient based on said diagnostic quantity and one or more of said quality of the fit and said quantity derived, to monitor severity of cardiac insufficiency of the patient.

10. The implantable medical system according to claim 9, wherein the data that describes the respiration are derived from signals detected by the pressure sensor.

11. The implantable medical system according to claim 9, wherein a value range of the signals of the activity sensor is subdivided into intervals having a specifiable length.

12. The implantable medical system according to claim 11, wherein a load stage is ascribed to at least one part of the intervals.

13. The implantable medical system according to claim 9, wherein the time-registration unit is configured to determine at least one time interval as a function of the load.

14. The implantable medical system according to claim 13, wherein the data that describes the respiration are evaluated for at least one part of the at least one time interval.

15. The implantable medical system according to claim 9, wherein the pressure sensor is disposed in a pulmonary artery of said patient.

16. The implantable medical system according to claim 9, wherein the data processing system is further configured to determine fit parameters of said at least two different fit functions or said fit function and start at least one action that depends on the fit parameters.

17. A method for monitoring respiratory parameters, comprising:
registering blood pressure values, at least temporarily from blood pressure signals at least temporarily and continuously detected by a pressure sensor of an implantable medical system, wherein said pressure sensor is disposed in a patient;
determining data describing a load by evaluating the blood pressure values that were registered;
determining data describing respiration by evaluating the blood pressure values that were registered from said blood pressure signals;
evaluating a dependence of the respiration on the data describing the load, or a dependence of the data describing the load on respiration and determining a diagnostic quantity that depends on data that describes the load using a data processing system of said implantable medical system,
wherein said data processing system is coupled with said pressure sensor and a time-registration unit of said implantable medical system, and,
wherein the determining the diagnostic quantity comprises
fitting of at least two different fit functions to a curve, wherein the curve describes a dependence of the respiration on the data that describes the load, or
a fit function is fit to the curve, wherein the curve describes the dependence of the respiration on the data that describes the load;
determining and evaluating a quality of the fit using said data processing system, wherein a type of shape of the fit, or a quantity derived from a vector of the quality of the fit, or both, is evaluated; and, determining a functional capacity of a cardiovascular system of the patient using said data processing system based on said diagnostic quantity and one or more of said quality of the fit and said quantity derived, to monitor severity of cardiac insufficiency of the patient; wherein said data processing system is configured to determine said functional capacity of the cardiovascular system of the patient.

18. A method for monitoring respiratory parameters, comprising:
registering signals from at least one activity sensor on an implantable medical system, at least temporarily, and determining data describing a load by evaluating the signals of the at least one activity sensor,
wherein said data comprises stress values and wherein said load comprises a physical load on a patient;
registering blood pressure values, at least temporarily from blood pressure signals at least temporarily and continuously detected by a pressure sensor of said implantable medical system, wherein said pressure sensor is disposed in said patient; determining data describing respiration by evaluating the blood pressure values that were registered from said blood pressure signals;
evaluating a dependence of the respiration on the data describing the load, or a dependence of the data describing the load on respiration and determining a diagnostic quantity that depends on data that describes the load using a data processing system of said implantable medical system,
wherein said data processing system is coupled with said activity sensor, said pressure sensor and a time-registration unit of said implantable medical system, and,
wherein the determining the diagnostic quantity comprises
fitting of at least two different fit functions to a curve, wherein the curve describes a dependence of the respiration on the data that describes the load, or a fit function is fit to the curve, wherein the curve describes the dependence of the respiration on the data that describes the load;
determining and evaluating a quality of the fit using said data processing system, wherein a type of shape of the fit, or a quantity derived from a vector of the quality of the fit, or both, is evaluated; and,
determining a functional capacity of a cardiovascular system of the patient using said data processing system based on said diagnostic quantity and one or more of said quality of the fit and said quantity derived, to monitor severity of cardiac insufficiency of the patient;
wherein said data processing system is configured to determine said functional capacity of the cardiovascular system of the patient.

19. A non-transitory computer-readable memory medium on which a program is stored wherein said program is configured to execute on a data processing device after said program has been loaded into a memory coupled with the data processing device wherein said program is configured to
register signals from at least one activity sensor of an implantable medical system, at least temporarily, and determine data that describe a load through evaluation of the signals of the at least one activity sensor,
wherein said data comprises stress values and wherein said load comprises a physical load on a patient;
register blood pressure values, at least temporarily from blood pressure signals at least temporarily and continuously detected by a pressure sensor of said implantable medical system, wherein said pressure sensor is disposed in said patient;
determine data that describe respiration through evaluation of the blood pressure values that were registered from said blood pressure signals;
evaluate a dependence of the respiration on the data that describes the load, or a dependence of the data that describes the load on respiration and determine a diagnostic quantity that depends on data that describes the load through use of a data processing system of said implantable medical system,
wherein said data processing system is coupled with said activity sensor, said pressure sensor and a time-registration unit of said implantable medical system, and,
wherein the diagnostic quantity is determined, through use of said data processing system, through
a fit of at least two different fit functions to a curve, wherein the curve describes a dependence of the respiration on the data that describes the load, or
a fit function is fit to the curve, wherein the curve describes the dependence of the respiration on the data that describes the load;
determine and evaluate a quality of the fit through use of said data processing system, wherein a type of shape of the fit, or a quantity derived from a vector of the quality of the fit, or both, is evaluated; and,
determine a functional capacity of a cardiovascular system of the patient based on said diagnostic quantity and one or more of said quality of the fit and said quantity derived, to monitor severity of cardiac insufficiency of the patient.

* * * * *